(12) United States Patent
Schoenmakers et al.

(10) Patent No.: US 9,618,460 B2
(45) Date of Patent: Apr. 11, 2017

(54) METHOD OF PERFORMING TOMOGRAPHIC IMAGING OF A SAMPLE IN A CHARGED-PARTICLE MICROSCOPE

(71) Applicant: FEI Company, Hillsboro, OR (US)

(72) Inventors: Remco Schoenmakers, Best (NL); David Foord, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/021,886

(22) Filed: Sep. 9, 2013

(65) Prior Publication Data

US 2014/0070095 A1   Mar. 13, 2014

Related U.S. Application Data

(60) Provisional application No. 61/699,975, filed on Sep. 12, 2012.

(30) Foreign Application Priority Data

Sep. 12, 2012   (EP) .................................... 12184099

(51) Int. Cl.
*G01N 23/04* (2006.01)
*G01N 23/225* (2006.01)
(Continued)

(52) U.S. Cl.
CPC ....... *G01N 23/046* (2013.01); *G01N 23/2251* (2013.01); *G06T 11/005* (2013.01);
(Continued)

(58) Field of Classification Search
None
See application file for complete search history.

(56) References Cited

U.S. PATENT DOCUMENTS 7,825,378 B2   11/2010   Yakushevska et al.
8,080,791 B2   12/2011   von Harrach et al.
(Continued)

FOREIGN PATENT DOCUMENTS

EP   1628321 B1   12/2009
EP   2063449 B1    4/2011
EP   2309459       4/2011

OTHER PUBLICATIONS

Saghi et al., "Hybrid Tomography or Nanostructures in the Electron Microscope", Mater. Res. Soc. Symp. Proc. vol. 1184, 2009.*
(Continued)

*Primary Examiner* — Wyatt Stoffa
*Assistant Examiner* — James Choi
(74) *Attorney, Agent, or Firm* — Scheinberg & Associates, P.C.; Michael O. Scheinberg; John E. Hillert (57) ABSTRACT

The invention relates to a method of performing tomographic imaging involving repeatedly directing a charged particle beam through a sample for a series of sample tilts to acquire a corresponding set of images and mathematically combining the images to construct a composite image. The latter of which consists of, at each of a second series of sample tilts, using a spectral detector to accrue a spectral map of said sample, thus acquiring a collection of spectral maps; analyzing said spectral maps to derive compositional data of the sample; and employing said compositional data in constructing said composite image.

20 Claims, 3 Drawing Sheets

(51) Int. Cl.
G06T 11/00 (2006.01)
H01J 37/28 (2006.01)
H01J 37/244 (2006.01)

(52) U.S. Cl.
CPC ........ H01J 37/28 (2013.01); *G01N 2223/419* (2013.01); *H01J 37/244* (2013.01); *H01J 2237/226* (2013.01); *H01J 2237/24485* (2013.01); *H01J 2237/24585* (2013.01); *H01J 2237/2611* (2013.01); *H01J 2237/2802* (2013.01); *H01J 2237/2807* (2013.01)

(56) References Cited

U.S. PATENT DOCUMENTS

| | | | |
|---|---|---|---|
| 8,232,523 | B2 | 7/2012 | Boughorbel et al. |
| 8,933,401 | B1* | 1/2015 | Reed ............... H01J 37/28 250/306 |
| 2006/0151708 | A1* | 7/2006 | Bani-Hashemi ...... G01T 1/2008 250/370.11 |
| 2007/0253612 | A1* | 11/2007 | Katayama ............ G01N 23/046 382/128 |
| 2010/0148064 | A1* | 6/2010 | Harrach et al. ............... 250/307 |
| 2011/0192976 | A1* | 8/2011 | Own et al. ..................... 250/311 |
| 2011/0278451 | A1 | 11/2011 | Tiemeijer et al. |
| 2012/0238870 | A1* | 9/2012 | Smith .................... A61B 6/025 600/431 |
| 2012/0292503 | A1 | 11/2012 | Phifer, Jr. et al. |
| 2013/0037714 | A1 | 2/2013 | Boughorbel et al. |
| 2013/0037715 | A1 | 2/2013 | Boughorbel et al. |
| 2013/0094716 | A1* | 4/2013 | Carpio ...................... G06T 5/50 382/109 |
| 2013/0188771 | A1* | 7/2013 | Kyriakou ............... A61B 6/032 378/19 |
| 2013/0228683 | A1 | 9/2013 | Boughorbel et al. |
| 2013/0259190 | A1* | 10/2013 | Walls .................... G01N 23/22 378/9 |

OTHER PUBLICATIONS

Reed, "Electron Microprobe Analysis and Scanning Electron Microscopy in Geology", Cambridge University Press, 2005.*

Yaguchi et al., "Observations of three-dimensional elemental distributions of a Si device using a 360°-tilt FIB and the cold field-emission STEM system", Ultramicroscopy 108 (2008).*

Florea et al., "3D Analysis of the Morphology and Spatial Distribution of Nitrogen in Nitrogen-Doped Carbon Nanotubes by Energy-Filtered Transmission Electron Microscopy Tomography", J. Am. Chem. Soc. 134 (2012).*

Burdet, Pierre, "Three Dimensional Microanalysis by Energy Dispersive Spectrometry: Improved Data Processing", École polytechnique fédérale de Lausanne, 2012.*

Florea, Ileana, et al., "3D Analysis of the Morphology and Spatial Distribution of Nitrogen in Nitrogen-Doped Carbon Nanotubes by Energy-Filtered Transmission Electron Microscopy Tomography," Journal of the American Chemical Society, 2012, pp. 9672-9680, vol. 134.

Saghi, Z., et al., "Hybrid Tomography of Nanostructures in the Electron Microscope," Mater. Res. Soc. Symp. Proc., 2009, 6 pgs, vol. 1184.

Unknown, "Particle-induced X-ray emission," Wikipedia (http://en.wikipedia.org/wiki/PIXE), retrieved Sep. 9, 2013, 4 pgs.

Unknown, "Evaluation of X-Ray Spectra Measured with Energy Dispersive Xray Spectrometer (EPMA)," Microanalyst.net (http://microanalyst.mikroanalytik.de/info2.phtml), retrieved Sep. 9, 2013, 9 pgs.

"Algebraic Reconstruction Technique," Wikipedia, Retrieved from the Internet Sep. 23, 2016, http://en.wikipedia.org/wiki/Algebraic_reconstruction_technique, 2 pages.

A.C. Kak and Malcolm Slaney, "Algorithms for Reconstruction with Nondiffracting Sources," Principles of Computerized Tomographic Imagino, IEEE Press, 1999, 64 pages.

Bangliang, S. et al., "An Improved Simultaneous Iterative Reconstruction Technique for Electrical Capacitance Tomography," 1st World Congress on Industrial Process Tomography, Buxton, Greater Manchester, Apr. 14-17, 1999, http://www.vcipt.org/pdfs/wcipt1/s2_1.pdf., 5 pages.

Batenburg, K.J. et al., "DART explained: how to carry out a discrete tomography reconstruction," Instrumentation and Methods, EMC 2008, vol. 1, pp. 295-296, Retrieved from the Internet Sep. 23, 2016; http://www.emat.ua.ac.be/pdf/1701.pdf.

Batenburg, K.J. et al., "DART: A practical reconstruction algorithm for discrete tomography," Retrieved from the Internet Apr. 9, 2015, http://homepages.cwi.nl/~kbatenbu/papers/basij_tip_2011.pdf, 25 pages.

C. Kubel et al., "Recent advances in electron tomograpy: TEM and HAADF-STEM tomography 7 for materials science and semiconductor applications," Microscopy and Microanalysis, Oct. 1, 2005, vol. 11, No. 5, pp. 378-400.

Gilbert, P., "Iterative methods for the three-dimensional reconstruction of an object from projections," Journal of Theoretical Biology, vol. 36, Issue 1, Jul. 1972, pp. 105-117.

Williams, P. et al., "Evaluation of Integrated Electrodes for Electrical Capacitance Tomography," 1st World Congress on Industrial Process Tomography, Buxton, Greater Manchester, Apr. 14-17, 1999, 7 pages.

* cited by examiner

METHOD OF PERFORMING TOMOGRAPHIC IMAGING OF A SAMPLE IN A CHARGED-PARTICLE MICROSCOPE

This Application claims priority from U.S. Provisional Application 61/699,975, filed Sep. 12, 2012, which is hereby incorporated by reference.

The invention relates to a method of performing tomographic imaging of a sample in a charged-particle microscope, comprising the following steps:
Providing a beam of charged particles;
Providing the sample on a sample holder that can be tilted relative to said beam;
Directing the beam through the sample and so as to form an image of the sample at an image detector;
Repeating this procedure at each of a first series of sample tilts so as to acquire a corresponding set of images;
Mathematically combining images from said set so as to construct a composite image.

The invention also relates to a charged-particle microscope comprising:
A charged-particle source, for producing a charged-particle beam;
A sample holder, for holding and positioning a sample;
A charged-particle lens system, for directing said beam through the sample so as to form an image of the sample;
An image detector, for detecting said image;
A spectral detector, for detecting a spectrum of the sample.

For purposes of clarity and consistency, the following terms as used throughout this text and the appended claims should be interpreted as follows:

The term "charged particle" encompasses an electron or ion (generally a positive ion, such as a Gallium ion or Helium ion, for example, though a negative ion is also possible). It may also be a proton, for example.

The term "charged-particle microscope" (CPM) refers to an apparatus that uses a charged-particle beam to create a magnified image of an object, feature or component that is generally too small to be seen in satisfactory detail with the naked human eye. In addition to having an imaging functionality, such an apparatus may also have a machining functionality; for example, it may be used to locally modify a sample by removing material therefrom ("milling" or "ablation") or adding material thereto ("deposition"). Said imaging functionality and machining functionality may be provided by the same type of charged particle, or may be provided by different types of charged particle; for example, a Focused Ion Beam (FIB) microscope may employ a (focused) ion beam for machining purposes and an electron beam for imaging purposes (a so-called "dual beam" microscope), or it may perform machining with a relatively high-energy ion beam and perform imaging with a relatively low-energy ion beam.

The term "sample holder" refers to any type of table, platform, arm, etc., upon which a sample can be mounted and held in place. Generally, such a sample holder will be comprised in a stage assembly, with which it can be accurately positioned in several degrees of freedom, e.g. with the aid of electrical actuators.

The term "charged-particle lens system" refers to a system of one or more electrostatic and/or magnetic lenses that can be used to manipulate a charged-particle beam, serving to provide it with a certain focus or deflection, for example, and/or to mitigate one or more aberrations therein. In addition to (various types of) conventional lens elements, the charged-particle lens system (particle-optical column) may also comprise elements such as deflectors, stigmators, multipoles, aperture (pupil) plates, etc.

The "series of different sample tilts" referred to here may take different forms. In particular, the tilt increments between successive members of such a series may be equal or unequal (or mixtures of these). Examples of scenarios with unequal tilt increments include EST (Equal Slope Tomography), in which the slope (tangent of tilt) undergoes equal increments, and the so-called Saxton tilt increment scheme, in which smaller tilt increments are used as one progresses toward larger tilt values (measured with respect to the sample surface). In addition to referring to the angle between the charged-particle beam and the plane of the sample surface (altitude angle), the term "tilt" may also refer to the azimuth angle, i.e. the rotational stance of the sample about the particle-optical axis intersecting it. A change in tilt value may thus encompass one or more discrete rotations of the sample about this axis (e.g. as in the case of so-called "dual axis", "multiple axis" and "conical tilt" tomography). The number of increments in a tilt series is generally discretionary.

Such concepts will be familiar to the skilled artisan.

In what follows, the invention will—by way of example—often be set forth in the specific context of electron microscopes. However, such simplification is intended solely for clarity/illustrative purposes, and should not be interpreted as limiting.

Electron microscopy is a well-known technique for imaging microscopic objects. The basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" beam of ions, allowing supportive activities such as ion-beam milling or ion-beam-induced deposition, for example. In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example. It should be noted that a STEM may be a dedicated tool, or it may be a TEM that is used in so-called "scanning mode" (enabled by the use of certain (dedicated) deflectors/detectors/software, for example).

The current invention is of relevance to CPMs in which the employed charged-particle beam passes through the sample, as in the case of a TEM or STEM, for example. In order to be (sufficiently) transmissive to the beam, the sample must be relatively thin (e.g. of the order of about a tenth of a micron to several microns, depending on the material involved) and the employed charged particles are generally accelerated to relatively high energies (e.g. of the order of about 1-500 keV, or even energies in the MeV range). The preparation, transport and storage of such thin samples present substantial technological challenges, particularly in the case of soft samples (e.g. biological tissue) and/or brittle samples (e.g. comprising crystalline material). However, difficult as these challenges currently are, they are bound to become even more difficult in the not-too-distant future, as technological advances in fields such as semiconductor manufacturing, mineralogy and microbiology will inevitably require ever thinner samples to be investigated. For example, the Semiconductor Roadmap for the coming five years foresees reductions of (some) Critical Dimensions in integrated circuits from 28 nm to as little as 10 nm and less, as new technologies and devices start to gain more prominence (e.g. as in the case of so-called FINFETs and Tri-Gate Transistors, stacked memories, nanowires, etc.). Performing satisfactory transmission microscopy on such structures may routinely require sample thicknesses of the order of 10 nm or less (so as to ensure that only a single layer of structures is being imaged, since ICs generally comprise stacked layers of such structures and, as the structures get smaller, so does the thickness of the layers). The production and handling of such sample thicknesses is likely to be fraught with substantial problems.

As an alternative to the use of very thin samples, one could contemplate performing tomographic transmission microscopy on a thicker sample. In this approach, because the employed sample is relatively thick, the charged particles transmitted through it will contain contrast information from various depths within the sample, so that the resulting image will be convoluted in terms of its depth information. In order to deconvolve this image, some form of parallax data will be required, so as to be able to distinguish between foreground and background features in the sample. Such parallax data can be provided by imaging the sample at a variety of different tilts with respect to the incoming charged-particle beam—which is equivalent to looking at the sample along a variety of different lines of sight. In order to perform the actual deconvolution of this tilt-differentiated set of images into a depth-resolved composite image, relatively advanced mathematical processing is required. Such processing is typically difficult and (very) time-consuming. When this is considered in addition to the considerable time needed to acquire the set of images in the first place (bearing in mind that a typical tomographic imaging session may entail the use of the order of 100 different tilt values, for example), then such a tomographic approach can start to look very unattractive.

It is an object of the invention to address these issues. More specifically, it is an object of the invention to provide a method that can be used to more efficiently perform transmission charged-particle microscopy on samples that comprise relatively thin structures. In particular, it is an object of the invention that such a method should not (generally) necessitate preparation of exceptionally thin samples. Moreover, it is an object of the invention that said method should be faster and/or more accurate than conventional tomographic transmission microscopy.

These and other objects are achieved in a method as specified in the opening paragraph, characterized by the following steps:

Selecting a second series of sample tilts;

At each of said second series of sample tilts, using a spectral detector to accrue a spectral map of said sample, thus acquiring a collection of spectral maps;

Analyzing said spectral maps to derive compositional data pertaining to the sample;

Employing said compositional data in constructing said composite image.

With regard to the terminology used here, the following should be noted:

Said second series ($S_2$) of sample tilts may be identical or different to said first series ($S_1$) of sample tilts. $S_2$ may be a subset of $S_1$. The members of $S_2$ may be (partially) interleaved with the members of $S_1$. The exact form and size of $S_2$ are discretionary, and can be tailored to a particular measurement set-up and/or measurement session.

The term "spectral map" should be interpreted as referring to a "map" of the sample in which some composition-dependent spectral measurand (e.g. particle energy, particle count, peak height, wavelength) is represented as a function of co-ordinate position on the sample.

Formation of an image and accrual of a spectral map may occur concurrently or successively (or in an interleaved fashion, for example). Concurrent spectral/image detection (i.e. for a/each tilt value that occurs in both $S_2$ and $S_1$, simultaneously forming an image and accruing a spectral map) is advantageous as regards throughput.

The fact that an image is formed as a consequence of passing a beam of particles through the sample does not restrict image formation to the use of transmitted particles; one may alternatively/supplementally form an image using scattered radiation, for example.

The method according to the present invention differs from known tomographic transmission microscopy in that the mathematical processing (de-convolution) step required to construct the desired composite image employs both contrast information from the set of (tilt-differentiated) images and compositional information from the attendant collection of spectral maps. The underlying philosophy here is that, by being able to form a compositional map of the sample, one can distill the location and form of the borders/transitional zones between regions of different composition. Since the composition of a region will generally influence its opacity to the employed charged-particle beam, such borders/transitional zones will also typically manifest themselves as contrast features in the set of images. Consequently, compositional information from said collection of spectral maps constitutes extra (rich) input into the mathematical processing step. Because there is more data available for the mathematical de-convolution procedure, it may be possible to decrease the chosen number of tilt values employed during data acquisition—thereby not only speeding up (and enriching) the mathematical processing step, but also tending to shorten the data acquisition step. This latter effect can be particularly pronounced in the case of "concurrent" spectral detection techniques, which can be performed simultaneously with the formation of the corresponding image; in other words, the spectral detector and image detector can do their work in parallel rather than sequentially. This aspect will receive more attention in the discussion below.

In a particular embodiment of the method according to the current invention, said accrual of spectral maps is performed using a technique selected from the group comprising EDX (Energy-Dispersive X-ray Spectroscopy; also sometimes referred to as EDS) and EELS (Electron Energy-Loss Spectroscopy), and the charged-particle microscope is a STEM. A STEM resembles a conventional TEM in that it employs transmissive microscopy, but it also somewhat resembles a SEM in that it builds up an image by scanning a relatively narrow charged-particle beam over a sample. This aspect of its operation lends itself to use with a technique such as EDX or EELS. This is because these techniques provide a cumulative spectrum of the whole "impingement area" of a sample that is intercepted at a given point in time by the incoming beam of charged particles; therefore, in order to generate a spatially resolved spectral map, it is best to scan a narrow beam over the sample and "stitch together" the individual spectra of the resulting array of small impingement areas. The EDX and EELS techniques provide compositional information as follows:

EDX: Here, a sample is bombarded with a narrow/focused input beam of charged particles (e.g. electrons). A lower-shell electron in an atom of the sample can be ejected from its orbit by a collision with one of these bombarding particles, creating an electron hole that is promptly filled by the de-excitation of a higher-shell electron in the atom in question, with the concurrent release of a quantum of energy in the form of an X-ray photon. The energy signature/distribution of photons emitted in this way will be characteristic of the particular electron shell structure of the atom in question, and can thus be used as a "fingerprint" in performing compositional analysis of the sample. An energy-dispersive spectrometric detector collects, sorts and counts the different photons of different energies, producing a measured spectrum for the area of the sample onto which the input beam was directed; such a spectrum can be rendered as a graph of counts per channel (ordinate) versus channel number (abscissa), corresponding to intensity versus energy, and generally comprising various peaks—whose energy can be used to identify the generating substance (element, material) and whose height can (in principle) be used to estimate relative quantity of the generating substance. One then moves the sample and/or the beam so that the beam is directed onto a new impingement area on the sample, and then repeats the process described above at said new area. Because EDX performs its spectral analysis on the basis of detected X-rays, it can be performed simultaneously with image formation on the basis of charged particles (such as electrons); it thus forms an example of "concurrent" spectral detection as alluded to above. It should be noted that, as employed in the present text/claims, the term EDX should be interpreted as encompassing so-called Wavelength Dispersive X-Ray Spectroscopy (WDX or WDS). This latter technique can be regarded as a particular refinement of EDX in which the X-rays emerging from a sample are filtered (e.g. with the aid of a particular type of crystal), so that only X-rays of a given wavelength are counted at any given time.

EELS: Here, a sample is bombarded with a narrow/focused input beam of electrons of a given input energy. Some of these electrons will undergo inelastic scattering in the sample, causing them to lose energy. The amount of this energy loss can be measured using an electron spectrometer, in which electrons emerging from the sample are caused to pass through an electromagnetic field that bends their paths towards a detector. The extent to which an electron's path is bent—and, thus, its arrival position on the detector—will depend on the electron's energy, and therefore also on the energy loss that it suffered at the sample. Although there are various possible causes of said energy loss (such as phonon and plasmon excitations, atomic inter- and intra-band transitions, and Čerenkov radiation production), the most important cause vis-à-vis EELS is atomic inner shell ionization, which is particularly useful for deducing the elemental components of the area of the sample impinged on by the input beam. Once EELS has been performed at a given impingement area on the sample, one moves the sample and/or the input beam so that the beam is directed onto a new area on the sample, and then repeats the process described above at said new area. It is possible to conduct EELS in a CPM in such a manner that it constitutes a "concurrent" spectral detection technique as alluded to above. In one such scenario, image formation can be conducted using a so-called Annular Dark Field (ADF) detector, which collects (peripheral) scattered electrons from the sample, allowing the electrons transmitted through the sample to be used by the EELS detector. In an alternative (or supplemental) scenario, a bright-field image is formed by collecting/registering a portion of the electrons that pass through the sample without undergoing substantial energy-loss or scattering; such a technique is set forth in more detail in US 2011/0278451 A1, for example (and also depicted in FIG. 3 below).

The skilled artisan in the field of electron microscopy will have basic familiarity with these techniques; however, their application in tomographic transmission microscopy as a means of assisting in the mathematical construction of a composite image is highly innovative.

In a particular refinement of the embodiment set forth in the previous paragraph, the employed technique is EDX and the spectral detector comprises a plurality of detection units disposed about the sample holder. The accumulation of an EDX spectrum can be a relatively slow process, since an EDX detector typically has only a relatively small detection cross-section (detector opening angle w.r.t. sample), and the detected flux of X-rays is generally relatively weak, necessitating a relatively long accumulation time. By disposing a plurality of detectors (e.g. four or more) in spatial distribution about the sample table, one serves to increase the cumulative detection cross-section presented to the X-ray flux, and thus serves to decrease the required accumulation time; as a result, an EDX measurement can then be performed "real time" together with image registration in the STEM, i.e. the former no longer acts as a timing bottleneck to slow down the latter. A multi-detector EDX set-up sec is described, for example, in U.S. Pat. No. 8,080,791, which is incorporated herein by reference.

In an alternative embodiment of the method according to the present invention, the employed CPM is an EFTEM (Energy-Filtered Transmission Electron Microscope). As explained above, electrons passing through a sample in a TEM can undergo a (variable) energy loss, so that the electrons traversing the sample will generally emerge with a range of energies. In an EFTEM, only a relatively narrow band of these energies is used (at any given time) to form an image. By forming such an image at a variety of such energy bands, one can thus acquire an energy-resolved set of images of the whole sample. Since, as explained above, each chosen energy band will be related to the atomic structure of particular materials in the sample, each registered image can also be seen as a spectral map of the sample, and a set of such images is concurrently a collection of spectral maps. This is thus an example of "concurrent" spectral detection as alluded to above.

Although various examples given up to now have involved electron microscopy, it should be noted—as stated above—that the current invention is intended to encompass charged particles other than electrons. For example, in a specific embodiment of the method according to the present invention, the employed CPM is a proton microscope and said accrual of spectral maps is performed using PIXE (Proton-Induced X-ray Emission). For more information on PIXE, see, for example: http://en.wikipedia.org/wiki/PIXE The compositional information acquired and applied in the method according to the current invention can be processed in various ways. Certain aspects of such processing will now be elucidated in more detail.

Making Elemental Maps:

As already discussed heretofore, the method according to the present invention acquires a collection of spectral maps (at different sample tilt values). Using known algorithms, a spectral map (which is essentially a two-dimensional, spatially-resolved grid of spectra) can be converted into a so-called elemental map (which is a two-dimensional, spatially-resolved grid of elements/materials). This is achieved using a procedure that iterates over all pixels in the grid of the spectral map. For each pixel, the spectrum taken at that pixel is analyzed for the presence of a particular (pre-selected) element (e.g. Si, Cu, etc.). This is done using spectral deconvolution algorithms. Basically, for all elements, their spectra are well known, i.e. one already knows for each element which peaks would occur if only that element were present. A measured spectrum is a convolution of an unknown number of elements. However, if one selects certain elements, these can be deconvolved from the raw spectrum to give a ratio of the quantity of these elements present. In this way, a particular elemental/compositional "label" can be attached to each pixel of a corresponding elemental map. For more information on this technique, reference is made to the following link: http://microanalyst.mikroanalytik.de/info2.phtml Conversion of a Sinogram into a Composite Image:

In tomography, a series of angular projections of an object is referred to as a sinogram. The current invention acquires a basic image sinogram (the set of images at different sample tilts) and also a supplementary elemental sinogram (the collection of elemental maps resulting from the procedure just discussed). In a process conventionally referred to as "reconstruction", each of these sinograms (or a "hybrid" sinogram composed of some members from each of the image and elemental sinograms) can be processed and converted into a corresponding composite image using various known mathematical techniques. For example:

SIRT: Simultaneous Iterative Reconstruction Technique.
See, for example:
http://www.vcipt.org/pdfs/wcipt1/s2_1.pdf
P. Gilbert, *Journal of Theoretical Biology*, Volume 36, Issue 1, July 1972, Pages 105-117.

DART: Discrete Algebraic Reconstruction Technique.
See, for example: http://en.wikipedia.org/wiki/Algebraic_reconstruction_technique
http://www.emat.ua.ac.be/pdf/1701.pdf, and references therein.

For detailed information, reference is made (for example) to the following well-known book:

A. C. Kak and Malcolm Slaney, *Principles of Computerized Tomographic Imaging*, IEEE Press, 1999.

In particular, chapter 3 of said book, especially sections 3.2 and 3.3, describes how the so-called Fourier Slice Theorem can be used as the basis for a reconstruction procedure.

Other well-known terms/techniques in the field of sinogram reconstruction include WBP (Weighted Back Projection) and POCS (projection Onto Convex Sets), for example.

The skilled artisan in the field of TEM tomography will be completely familiar with these and other mathematical reconstruction techniques. However, their application to corresponding/complementary elemental sinograms and image sinograms is highly innovative.

In a particular embodiment of a method according to the present invention, the number of different sample tilts employed in acquiring said set of images is chosen inter alia on the basis of an analysis of said spectral maps. Such an embodiment can take many possible forms. For example:

One could use an iterative approach. Here, in a first measurement run, the inventive method is performed using a given "standard" number of image tilts, e.g. 121 tilt values in equal 1-degree increments from +60 degrees to −60 degrees (measured from the sample surface). Based inter alia on the ease with which a composite image can be reconstructed (using the additional spectral map data provided by the invention), one can elect to use a smaller number of tilt values (e.g. 25% fewer values) in a next iterative run. And so forth, until one achieves a number of tilt values that is considered to be (roughly) optimal for a particular type/category of sample/investigation; this value can then be used for future measurement runs of the same type/category. Such an embodiment represents an à posteriori approach.

Alternatively, one could use an on-the-fly approach, whereby a processor examines elemental maps and images as they are acquired and uses pre-selected criteria (e.g. observed signal-to-noise ratio, observed edge raggedness, diversity of observed elements/materials, distribution pattern of elements/materials, regularity of observed features, etc.) to adjust (downward or upward) an initially chosen number of tilt values.

The invention will now be elucidated in more detail on the basis of exemplary embodiments and the accompanying schematic drawings, in which.

In the Figures, where relevant, corresponding parts are indicated using corresponding reference symbols.

EMBODIMENT 1

Figure 1:
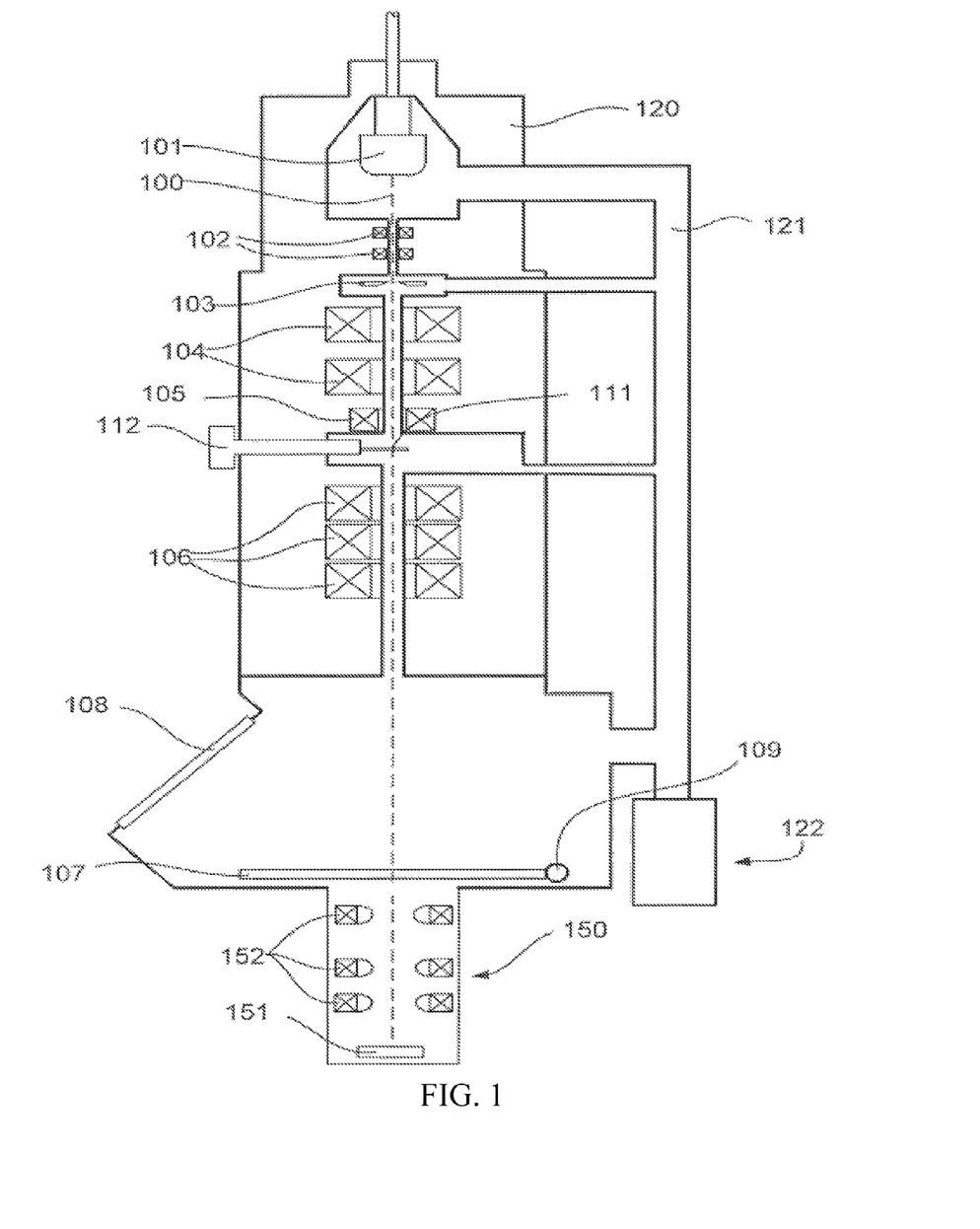
FIG. 1 renders a longitudinal cross-sectional view of part of a charged-particle microscope (TEM) in which a method according to the present invention can be enacted.

FIG. 1 renders a highly schematic longitudinal cross-sectional view of a particular embodiment of a CPM in which the current invention can be applied. In the present instance, the CPM is a TEM.

The depicted TEM comprises a vacuum housing 120 that is evacuated via tube 121 connected to a vacuum pump 122. A particle source in the form of an electron gun 101 produces a beam of electrons along a particle-optical axis (imaging axis) 100. The electron source 101 can, for example, be a field emitter gun, a Schottky emitter, or a thermionic electron emitter. The electrons produced by the source 101 are accelerated to an adjustable energy of typically 80-300 keV (although TEMs using electrons with an adjustable energy of 50-500 keV, for example, are also known). The accelerated electron beam then passes through a beam limiting aperture/diaphragm 103 provided in a platinum sheet. To align the electron beam properly to the aperture 103, the beam can be shifted and tilted with the aid of deflectors 102, so that the central part of the beam passes through the aperture 103 along axis 100. Focusing of the beam is achieved using magnetic lenses 104 of a condenser system, together with (part of the) final condenser lens 105. Deflectors (not depicted) are used to center the beam on a region of interest on a sample, and/or to scan the beam over the surface of the sample. In this schematic, functional depiction, the deflectors 102 are shown relatively high up in the CPM, and final condenser lens 105 is shown as being relatively small; however, the skilled artisan will appreciate that deflectors 102 may be much lower in the CPM (e.g. nested within the lens 105), and that item 105 may be much larger than depicted.

The sample to be examined is held by a sample holder 112 in such a manner that it can be positioned in the object plane 111 of projection system 106 (whose uppermost lens element is conventionally referred to as an objective lens). The sample holder 112 may offer various positional/motional degrees of freedom (one or more of translation(s), pitch, roll and yaw), and may also have temperature control functionality (heating or cryogenic). It may be a conventional type of sample holder for holding a static sample in a containment plane; alternatively, the sample holder 112 can be of a special type that accommodates a moving sample in a flow plane/channel that can contain a stream of liquid water or other solution, for example.

The sample is imaged by projection system (projection lens system, projection column) 106 onto fluorescent screen 107, and can be viewed through a window 108. The enlarged image formed on the screen typically has a magnification in the range $10^3 \times$-$10^6 \times$, and may show details as small as 0.1 nm or less, for example. The fluorescent screen 107 is connected to a hinge 109, and can be retracted/folded away such that the image formed by the projection system 106 impinges upon image detector 151. It is noted that, in such an instance, the projection system 106 may need to be (slightly) re-focused so as to form the image on the image detector 151 instead of on the fluorescent screen 107. It is further noted that the projection system 106 may additionally form intermediate images at intermediate image planes (not depicted).

The image detector 151 may, for example, comprise a Charge-Coupled Device (CCD) or a Complementary Metal Oxide Semiconductor (CMOS) device, both of which can be used to detect impinging electrons. As an alternative to electron detection, one can also use a CCD/CMOS that detects light—such as the light emitted by a Yttrium Aluminium Garnet (YAG) crystal (for example) that is bonded to the CCD/CMOS, or connected thereto by optical fibers (for example). In such an indirect detector, the YAG crystal emits a number of photons when an electron hits the crystal, and a portion of these photons is detected by the CCD/CMOS; in direct detectors, electrons impinge on the semiconductor chip of the CCD/CMOS and generate electron/hole pairs, thereby forming the charge to be detected by the CCD/CMOS. The detector 151 is connected to a processing apparatus (controller) and display unit [not depicted].

The image formed on the fluorescent screen 107 and on the image detector 151 is generally aberrated due (for example) to imperfections produced in the projection system 106. To correct such aberrations, various multipoles can be deployed in/near the projection system 106. Such multipoles are not depicted in FIG. 1, so as to avoid cluttering the drawing, but the skilled artisan will be familiar with their design, positioning and implementation.

It should be noted that FIG. 1 only shows a schematic rendition of a (simplified) TEM, and that, in reality, a TEM will generally comprise many more deflectors, apertures, etc.

In the context of the current invention, the illustrated TEM will also be provided with a spectral detector, in which case the following situations can be distinguished:

EFTEM: If the TEM is used as an EFTEM, then the image detector 151 will also play the role of spectral detector, as set forth above. In such a CPM, use will be made of an energy "filter", whose purpose is to select which energy range of electrons will be admitted to the detector 151 at any given time. This filter is schematically indicated here by the deflection coils 152, which will "pass" certain electron energies while deflecting others aside.

Figure 2:
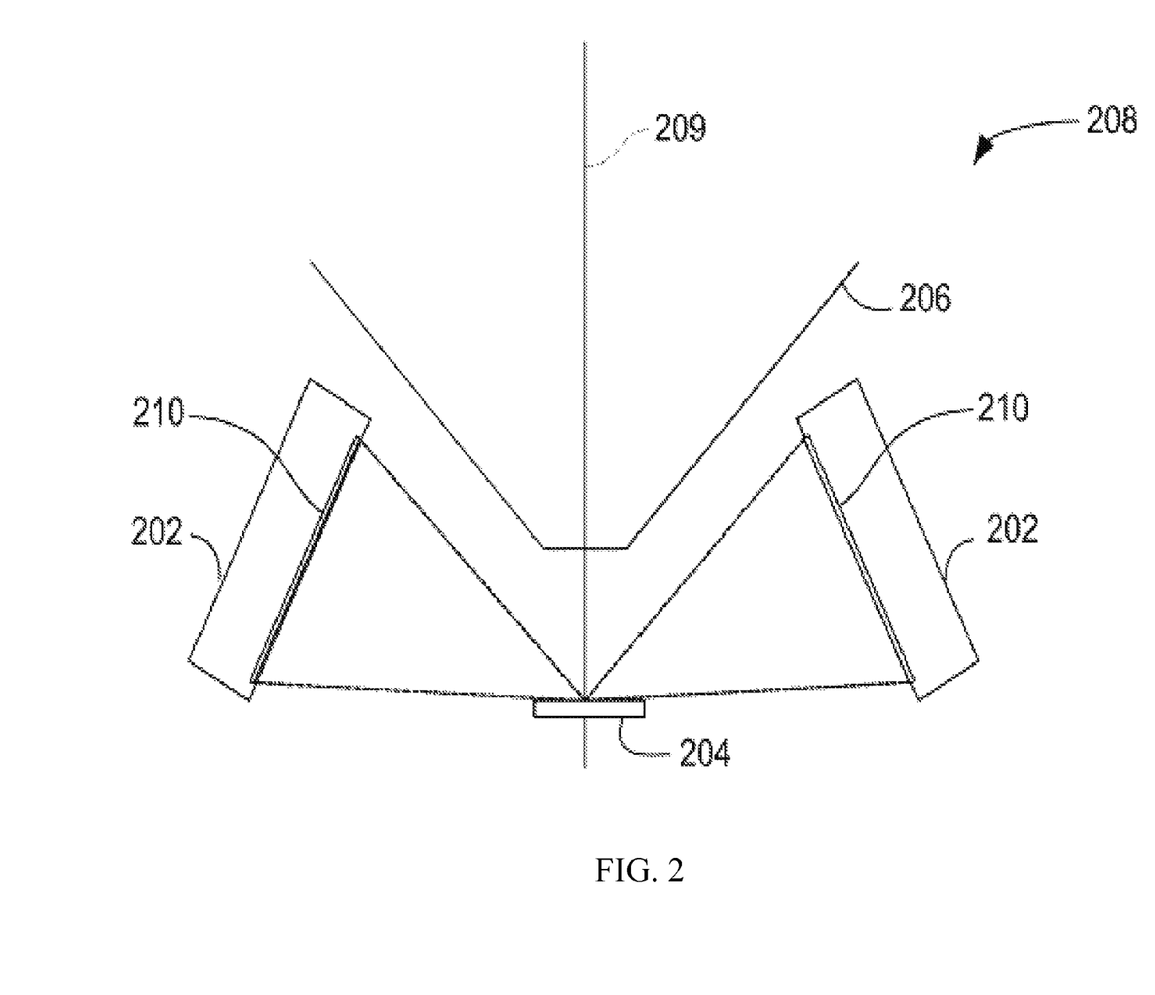
FIG. 2 renders a longitudinal cross-sectional view of part of an EDX detector arrangement in a charged-particle microscope in which a method according to the present invention can be enacted.

EDX: As an alternative (or supplement), the illustrated TEM can make use of EDX as a spectral detection technique. In this respect, FIG. 2 renders a longitudinal cross-sectional view of part of an EDX detector arrangement that can be used for this purpose in a CPM. The partially depicted CPM 208 has a particle-optical axis 209 which intercepts a sample 204 below a pole piece 206 of a charged-particle lens (not depicted). As here illustrated, two EDX detectors 202 are positioned on opposite sides of the sample 204; however, this is a matter of choice, and more detectors (e.g. four) or just one such detector may instead be employed. In a particular embodiment, an active area 210 of each detector 202 preferably subtends a solid angle of about 0.25 steradian or more with respect to the sample 204. Each detector 202 preferably detects X-rays at take-off angles of less than about 50 degrees (referenced to a horizontal plane) from the surface of the sample 204, and more preferably at take-off angles in the range 5-35 degrees; such low take-off angles tend to reduce possible detector damage from backscattered electrons, while maintaining a relatively low level of background Bremsstrahlung radiation in the acquired spectra, and also helping to make the most of available space in the sample vicinity. As already set forth above, when EDX is used for spectral detection, the depicted TEM can be used in STEM mode.

EELS: As a further alternative (or supplement), the illustrated TEM can make use of EELS as a spectral detection technique. To this end, the deflection coils 152 can be used to deflect transmitted electrons (traversing the sample) in a direction away from the optical axis 100 and toward an off-axis EELS detector; this is not shown in FIG. 1, but is illustrated in detail in FIG. 3. As regards image detection, different possibilities can be considered. For example:

Transmitted electrons can be allowed to pass unhindered through the coils 152 to the image detector 151 (see FIG. 1). Such a scenario does not lend itself to "concurrent" spectral detection/image formation as alluded to above.

Figure 3:
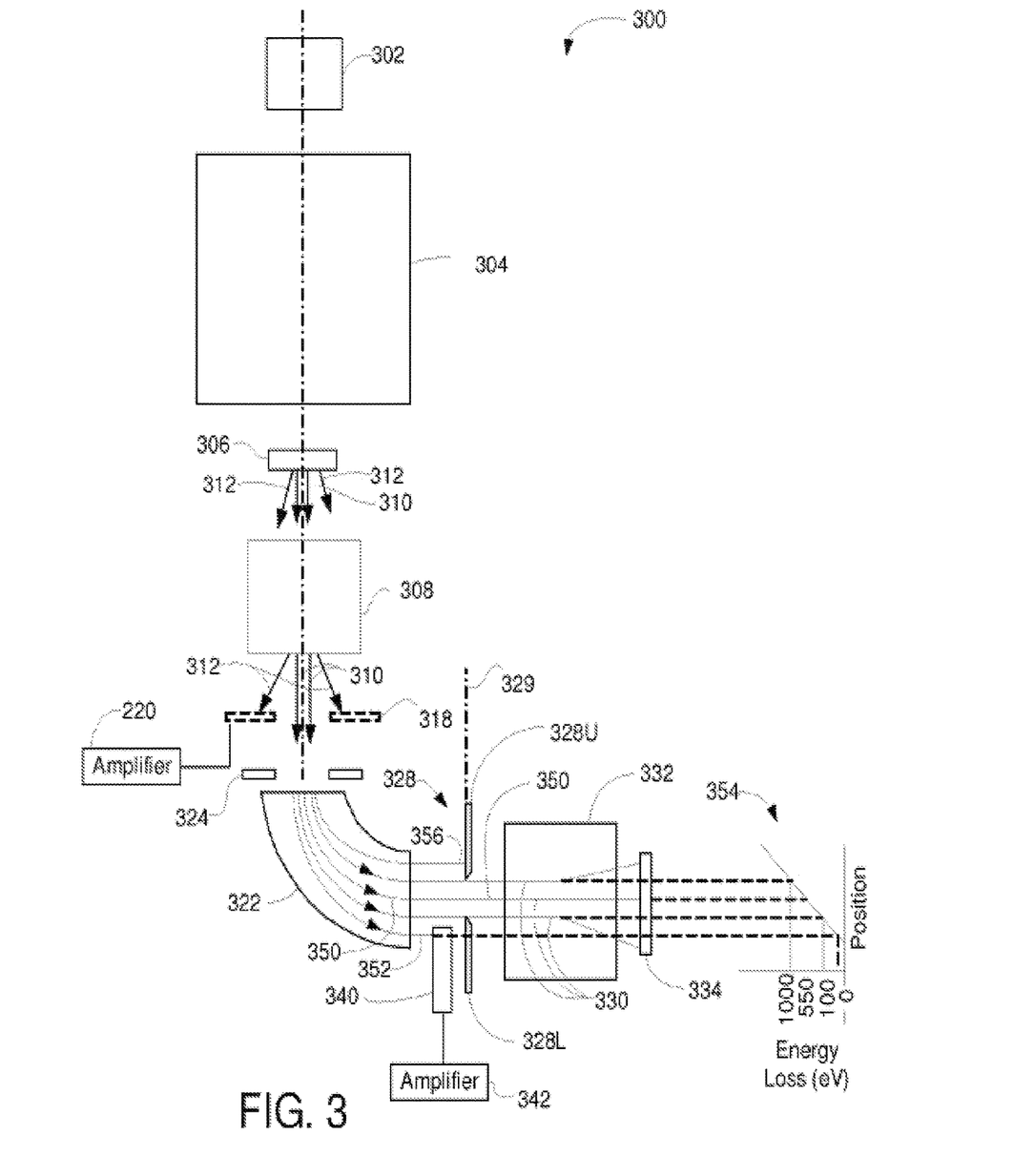
FIG. 3 renders a longitudinal cross-sectional view of part of an EELS detection set-up in a STEM in which a method according to the present invention can be enacted.

Alternatively, with reference to FIG. 3, use of a dedicated dark-field detector (318) and/or bright-field detector (340) does allow "concurrent" spectral detection/image formation. In this context, FIG. 3 shows a STEM 300 comprising an electron source 302, illumination system 304, sample 306 and projection system 308. An ADF detector set-up 318, 220 can be used to collect scattered electrons 312 and use them to form a dark-field electron image. On the other hand, bright-field electrons 310 pass through an aperture 324 into an electron dispersion system (prism) 322, where they are "fanned out" into an energy-resolved distribution 352, 350, 356. Adjustable aperture plates 328U, 328L allow the central core 350 of this distribution through, while blocking its edge portions 352, 356. The edge portion 352 comprises electrons that have suffered relatively low energy loss, and these can be collected by detector set-up 340, 342 to form a bright-field electron image. On the other, the central core 350 traverses optical system 332, which directs electron beams 330 onto different positions on detector 334, depending on their energy. In this way, EELS spectral information is obtained.

As already set forth above, when EELS is used for spectral detection, the TEM of FIG. 1 can be used in STEM mode.

The next Embodiment will explain how a specific example of a method according to the present invention can be enacted.

EMBODIMENT 2

In this Embodiment, it will be assumed that use is made of the TEM of FIG. 1, configured to operate in scanning mode (STEM). A particular example of a method according to the present invention might then comprise the following steps:

(a) One chooses a first series $S_1$ of tilt values. For example, a series of 101 tilt values from −50 degrees to +50 degrees in equal increments of 1 degree. Each tilt in this series $S_1$ can be achieved by appropriately actuating the sample holder 112 of FIG. 1 (onto which an appropriately thin sample has been mounted).

(b) One chooses a second series $S_2$ of tilt values. In this particular case, $S_2$ is a sub-series of Si, i.e. certain tilt values will occur in both Si and $S_2$, whereas others will occur only in $S_1$. However, as set forth above, this particular embodiment of $S_2$ is purely discretionary, and other possibilities could also be conceived, e.g. $S_2=S_1$.

(c) For each tilt value that is a member of Si, one scans the electron beam in a raster pattern across the surface of the sample and forms an image of the sample on detector 151. This image is stored. In this way, a set (sinogram) of images is acquired.

(d) If a given tilt value is also a member of $S_2$, then one also accrues a spectral map of the sample at that tilt value—once again during scanning motion of the electron beam in a raster pattern across the surface of the sample. It is efficient to accrue this spectral map concurrently/simultaneously with formation of the image in (c), though this is not strictly required. In this way, a collection (sinogram) of spectral maps is acquired. These spectral maps may be acquired using techniques such as EDX, EELS, EFTEM, etc. (see above).

(e) One converts the spectral maps from step (d) into corresponding elemental maps.

(f) If desired, one can form a "hybrid" sinogram by mixing certain elements from the sinogram in (c) with certain elements from the sinogram in (e).

(g) One performs a mathematical reconstruction algorithm on the sinograms resulting from steps (c) and (e) [alternatively on the "hybrid" sinogram resulting from optional step (f)], thus constructing a composite image (tomogram) of the sample.

As regards items (c) and (d) above, but also as a general comment pertaining to the invention as a whole, it should be noted that the measurement/dwell time associated with each member of $S_2$ (spectral maps) need not be the same as that associated with members of $S_1$ that are not in $S_2$ (images). For example:

If only an image needs to be formed at a particular tilt value, then this can be done with a relatively short measurement/dwell time.

On the other hand, if a spectral map has to be accrued at a particular tilt value, then one may choose a longer measurement/dwell time, so as to secure a better signal-to-noise ratio, for example.

The skilled artisan will readily grasp this aspect of the invention, and will be able to choose relative dwell times depending on the apparatus/sample that he is employing.

We claim as follows:

1. A method of performing tomographic imaging of a sample in a charged-particle microscope, comprising:
   providing a beam of charged particles;
   providing the sample on a sample holder that can be tilted relative to said beam;
   directing the beam through the sample and so as to form an image of the sample at an image detector;
   repeating this procedure at each of a first series of sample tilts so as to acquire a corresponding set of images, wherein the set of images contains contrast information from various depths within the sample that is convoluted with respect to depth;
   using a spectral detector to accrue a spectral map of said sample for each tilt of a second series of sample tilts, thus acquiring a collection of spectral maps;
   using a processing apparatus to:
   analyze said spectral maps to derive compositional data pertaining to the sample;
   deconvolve the set of images by mathematically deconvolving the contrast information with respect to depth using the compositional data; and
   construct a depth-resolved composite image of the sample from the deconvoluted set of images,
   wherein using the compositional data reduces the overall time required to perform the tomographic imaging by reducing a mathematical processing time required to construct the depth-resolved composite image, the mathematical processing time being the time required for the processing apparatus to carry out the mathematical deconvolution of the contrast information.

2. The method of claim 1, wherein said accrual of spectral maps is performed using a technique selected from the group comprising Energy-Dispersive X-ray Spectroscopy and Electron Energy-Loss Spectroscopy, and the charged-particle microscope is a Scanning Transmission Electron Microscope.

3. The method of claim 2, wherein said technique is EDX and said spectral detector comprises a plurality of detection units disposed about the sample holder.

4. The method of claim 1, wherein said charged-particle microscope is an Energy-Filtered Transmission Electron Microscope.

5. The method of claim 1, wherein said charged-particle microscope is a proton microscope and said accrual of spectral maps is performed using Proton-Induced X-ray Emission.

6. The method of claim 1, wherein said image detector and said spectral detector are operated simultaneously for at least one sample tilt common to both said first series and said second series of sample tilts.

7. The method of claim 1, wherein the number of different sample tilts employed in acquiring said set of images is chosen on the basis of an analysis of said spectral maps.

8. A charged-particle microscope comprising:
   a charged-particle source, for producing a charged-particle beam;
   a sample holder, for holding and positioning a sample;
   a charged-particle lens system, for directing said beam through the sample so as to form an image of the sample;
   an image detector, for detecting said image; and
   a spectral detector, for detecting a spectrum of the sample, which charged-particle microscope is constructed and arranged to perform the method of claim 1.

9. The method of claim 1 in which the second series of sample tilts may be identical to, different from, or partially interleaved with said first series of sample tilts.

10. The method of claim 1 in which formation of an image and accrual of a spectral map may occur concurrently or successively.

11. A charged-particle microscope comprising:
   a charged-particle source, for producing a charged-particle beam;
   a sample holder, for holding and positioning a sample;
   a charged-particle lens system, for directing said beam through the sample so as to form an image of the sample;
   an image detector, for detecting said image;
   a spectral detector, for detecting a spectrum of the sample, a processing apparatus controller including instructions comprising:

directing a beam of charged particles through a sample and so as to form an image of the sample at the image detector, the sample being on the sample holder that can be tilted relative to said beam;

repeating this procedure at each of a first series of sample tilts so as to acquire a corresponding set of images containing contrast information from various depths within the sample that is convoluted with respect to depth;

using a spectral detector to accrue a spectral map of said sample for each tilt of a second series of sample tilts, thus acquiring a collection of spectral maps;

analyzing said spectral maps to derive compositional data pertaining to the sample; and deconvolving the set of images by mathematically deconvolving the contrast information with respect to depth using the compositional data; and constructing a depth-resolved composite image of the sample from the deconvoluted set of images, wherein using the compositional data reduces the overall time required to perform the tomographic imaging by reducing a mathematical processing time required to construct the depth-resolved composite image, the mathematical processing time being the time required for the processing apparatus to carry out the mathematical deconvolution of the contrast information.

12. The charged-particle microscope of claim 11, wherein said accrual of spectral maps is performed using a technique selected from the group comprising Energy-Dispersive X-ray Spectroscopy and Electron Energy-Loss Spectroscopy, and the charged-particle microscope is a Scanning Transmission Electron Microscope.

13. The charged-particle microscope of claim 12, wherein said technique is EDX and said spectral detector comprises a plurality of detection units disposed about the sample holder.

14. The charged-particle microscope of claim 11, wherein said charged-particle microscope is an Energy-Filtered Transmission Electron Microscope.

15. The charged-particle microscope of claim 11, wherein said charged-particle microscope is a proton microscope and said accrual of spectral maps is performed using Proton-Induced X-ray Emission.

16. The charged-particle microscope of claim 11, wherein said image detector and said spectral detector are operated simultaneously for at least one sample tilt common to both said first series and said second series of sample tilts.

17. The charged-particle microscope of claim 11, wherein the number of different sample tilts employed in acquiring said set of images is chosen on the basis of an analysis of said spectral maps.

18. The method of claim 1, wherein using the compositional data reduces the overall time required to perform the tomographic imaging by reducing a mathematical processing time required to construct the depth-resolved composite image compared to a method that constructs an equivalent depth-resolved composite image of the sample without acquiring and using the compositional data.

19. The method of claim 1, wherein using the compositional data reduces the overall time required to perform the tomographic imaging by reducing the number of sample tilts required to construct the depth-resolved composite image.

20. The charged-particle microscope of claim 11, wherein using the compositional data reduces the overall time required to perform the tomographic imaging by reducing a mathematical processing time required to construct the depth-resolved composite image compared to a method that constructs an equivalent depth-resolved composite image of the sample without acquiring and using the compositional data.

* * * * *